United States Patent [19]
Stoop et al.

[11] Patent Number: 6,161,041
[45] Date of Patent: Dec. 12, 2000

[54] PACEMAKER SYSTEM WITH DIURNAL PATTERN CONTROLLED OVERDRIVE FOR PREVENTION OF TACHYCARDIA

[75] Inventors: Gustaaf A. P. Stoop; Bernhard De Vries, both of Dieren, Netherlands

[73] Assignee: Vitatron Medical B. V., Dieren, Netherlands

[21] Appl. No.: 09/179,043

[22] Filed: Oct. 26, 1998

[51] Int. Cl.$^7$ .......................... A61N 1/365; A61N 1/362
[52] U.S. Cl. .............................. 607/14; 607/25
[58] Field of Search ................ 607/14, 25; 600/516

[56] References Cited

U.S. PATENT DOCUMENTS

| | | | |
|---|---|---|---|
| 4,972,834 | 11/1990 | Begemann et al. | 600/516 |
| 5,042,497 | 8/1991 | Shapland | 607/14 |
| 5,271,393 | 12/1993 | Callaghan | 607/14 |
| 5,560,368 | 10/1996 | Berger | 128/703 |
| 5,861,011 | 1/1999 | Stoop | 607/25 |
| 5,978,711 | 11/1999 | Van Hove | 607/25 |

OTHER PUBLICATIONS

Christiansen et al., "Difference in QT Interval Measurement on Ambulatory ECG Compared With Standard ECG," PACE, vol. 19, Sep. 1996, pp. 1296–1302.

Van Leeuwen et al., "Spatial Distribution of QT Intervals; An Alternative Approach to QT Dispersion," PACE, vol. 19, Nov. 1996, Part II, pp. 1894–1899.

Horii et al., "Changes of Heart Rate and QT Interval at High Altitude in Alpinists: Analysis by Holter Ambultory Electrocardiogram," Clinical Cardiology 1987, 10:238–242.

Bexton et al., "Diurnal Variation of QT Interval—Influence of the Autonomic Nervous System," British Heart Journal 1986; 55:253–258.

Rasmussen et al., "QT Interval in 24–Hour Ambulatory ECG Recordings From 60 Healthy Adult Subjects," J. Electrocardiology 1991; 24:91–95.

Browne et al., "Prolongation of the Q–T Interval in Man During Sleep," Amercian Journal of Cardiology Jul. 1983; 52:55–59.

Murakawa, Yuji et al., "Role of Sympathovagal Interaction in Diurnal Variation of QT Interval," The American Journal of Cardiology, vol. 69, Feb. 1, 1992, pp. 339–343.

Molnar et al., "Diurnal Pattern of QTc Interval: How Long is Prolonged?" American College Cardiology 1996; 27:76–83.

*Primary Examiner*—Carl H. Layno
*Attorney, Agent, or Firm*—Thomas F. Woods; Harold Patton; Michael J. Jaro

[57] ABSTRACT

There is provided a cardiac pacemaker system with a ventricular tachycardia prevention feature, whereby the pacemaker monitors ventricular activity during each patient awakening period to determine when VT is likely. In a preferred embodiment, QRS and T wave templates are generated cyclically during awakening, and compared to normal templates to obtain a measure of variability, indicative of refractory dispersion and thus of probable VT. Ventricular extra-systoles are also monitored and analyzed during the awakening period to see how closely they occur to the ventricular vulnerable period. When the monitored data indicates VT probability during awakening, the pacemaker responds by overdriving the heart with an intervention pacing rate which is continually adjusted as a function of the currently obtained data.

20 Claims, 5 Drawing Sheets

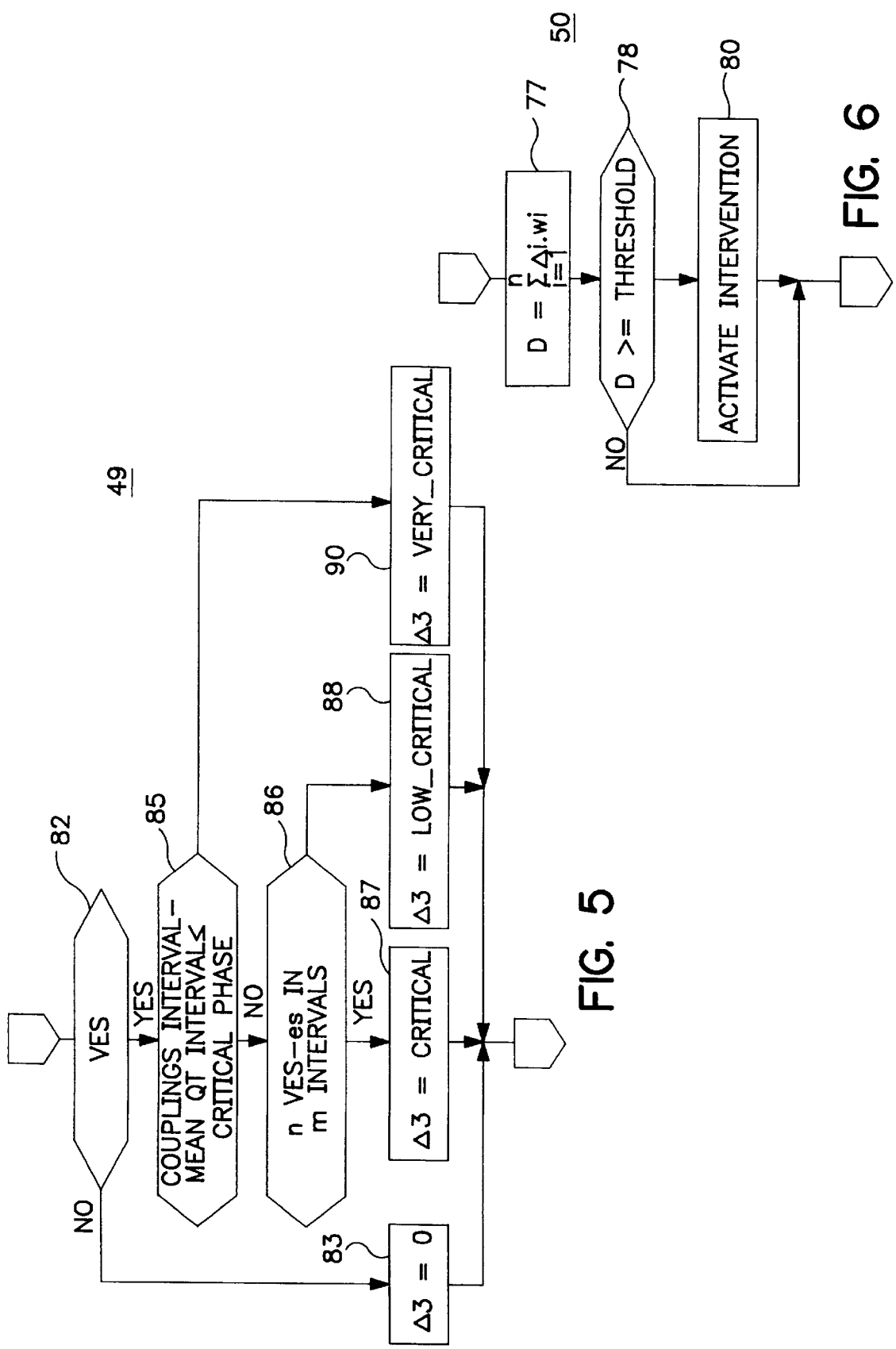

PACEMAKER SYSTEM WITH DIURNAL PATTERN CONTROLLED OVERDRIVE FOR PREVENTION OF TACHYCARDIA

FIELD OF THE INVENTION

This invention relates to cardiac pacemaker systems and, more particularly, cardiac pacemaker systems with techniques for anticipating tachycardia and the capacity to automatically switch to a pacing modality designed to prevent Ventricular Tachycardia.

BACKGROUND OF THE INVENTION

The prevention of ventricular tachycardia and other dangerous arrhythmias has become a subject of intensive study and research. Ventricular tachycardia (VT) is a lethal arrhythmia which is known to frequently lead to sudden death, usually after progressing to ventricular fibrillation (VF). As a result, there have been many investigations into techniques for monitoring a patient's cardiac condition to determine when conditions indicate a likelihood of VT, and to otherwise continually assess the risk of VT and VF.

It is known that QT interval, and in particular abnormalities of the QT interval, are associated with ventricular arrhythmias, e.g., in long QT syndromes and after myocardia infarction. See "Diurnal Variation of the QT Interval—Influence of the Autonomic Nervous System," Bexton et al., *British Heart J.*, 1986; 55:253–8. Thus, the QT interval of the surface EKG is accepted as an indirect measure of patient myocardial depolarization and repolarization. It is known that QT is longer during sleep, and in fact QT corrected for rate (QTc) is also longer during sleep. Further, it has been noted that QTc interval and QTc variability reach peak shortly after awakening hours, which may reflect increased automatic instability during early waking hours; and further that the time of the peak value corresponds to the period of reported increased vulnerability to ventricular tachycardia and sudden cardiac death. Molnar et al., *J Am. Coll. Cardiology*, 1996 Jan., 27:1, 76–83. See also Christenson et al., *PACE*, Vol. 19, September 1996, 1296–1393, stating that QTc exhibits significant diurnal variability. The literature suggests that there are significant changes in the autonomic system during sleep, with either an increase in para-sympathetic tone, or an increase in sympathetic activity, or both. There is also a diurnal variation in circulating catecholamines, and specifically the catecholamine level drops during the night. These factors are known to influence repolarization, nighttime variations of which are reflected in the lengthening QT interval, and lengthened QTc. Other investigations have looked into the temporal and spatial distribution of QT intervals, and suggest that QT dispersion (QTd), measured as the difference between the maximal and minimal value of QT duration, can be associated with increased risk of ventricular tachycardia and sudden cardiac death. Accordingly, the literature presently suggests that both QT interval prolongation and increased QT dispersion (refractory dispersion), or dispersion of the repolarization duration, are important reflectors of the risk of an incipient ventricular tachycardia.

This invention is responsive to the need to address the increased vulnerability to attacks of VT during or just after the waking period, and utilize the fact that the awakening period is characterized by observable variabilities of the depolarization and repolarization waves and the QT duration. In particular, the invention meets the need for a pacemaker which incorporates the capacity to monitor the diurnal heart pattern, particularly changes of the QRS-T waveform during the awakening period, so as to provide an indication of a risk of VT. A pacemaker in accordance with this invention also automatically provides for a controlled pacing response designed to prevent the onset of VT during the vulnerable awakening period.

SUMMARY OF THE INVENTION

It is a primary object of this invention to provide a pacemaker system having diurnal pattern detection for determining, on the basis of monitored QT interval, a period of patient awakening which covers the period when cardiac patients are most vulnerable to onset of VT; and to combine in the pacemaker system a continuous determination throughout the awakening period of data indicative of the likelihood of incipient VT, combined with a pacing response mode for preventing VT when it is determined to be likely.

In accordance with the above objects, there is provided a pacemaker system having a ventricular prevention feature which is activated during patient awakening, and which provides for ventricular tachycardia prevention pacing dependent upon information obtained from sensed QRS-T complexes before and during awakening. The pacemaker has a normal learning routine operative during the non-awakening hours, during which it obtains and continuously updates and stores representative templates for the patient ventricular depolarization (QRS) and repolarization (T wave). Awakening is determined by monitoring changes in QT interval, and an awakening period is timed out. During an awakening period, the pacemaker cyclically obtains and compares the current depolarization and repolarization templates to the respective stored representative templates to obtain a measure of template deviations, and thus dispersion variability; and gathers data relating to the occurrence of each ventricular extra systole (VES) and its coupling interval relative to the patient mean QT interval. On the basis of this data, it is determined whether intervention is indicated, i.e., should the pacemaker go into an overdrive mode to capture and control the ventricular beats.

During activation of the intervention mode, the pacemaker delivers pacing pulses at an intervention rate which is above the current spontaneous rate, to decrease the dispersion in cardiac refractoriness. The intervention overdrive rate is incremented up or down cyclically to adjust for changes in variability as measured by the template and VES data. Whenever the awakening period is over, the intervention mode is left and the pacemaker returns to the learning phase, and normal handling.

BRIEF DESCRIPTION OF THE DRAWINGS

FIG. 5 is a simplified flow diagram illustrating the primary steps taken in carrying out the Ventricular Extra Systole analysis portion of the VT Prevention Routine.

FIG. 6 is a simplified flow diagram illustrating the primary steps taken in carrying out the Determine Intervention portion of the VT Prevention routine.

DESCRIPTION OF THE PREFERRED EMBODIMENTS

Figure 1:
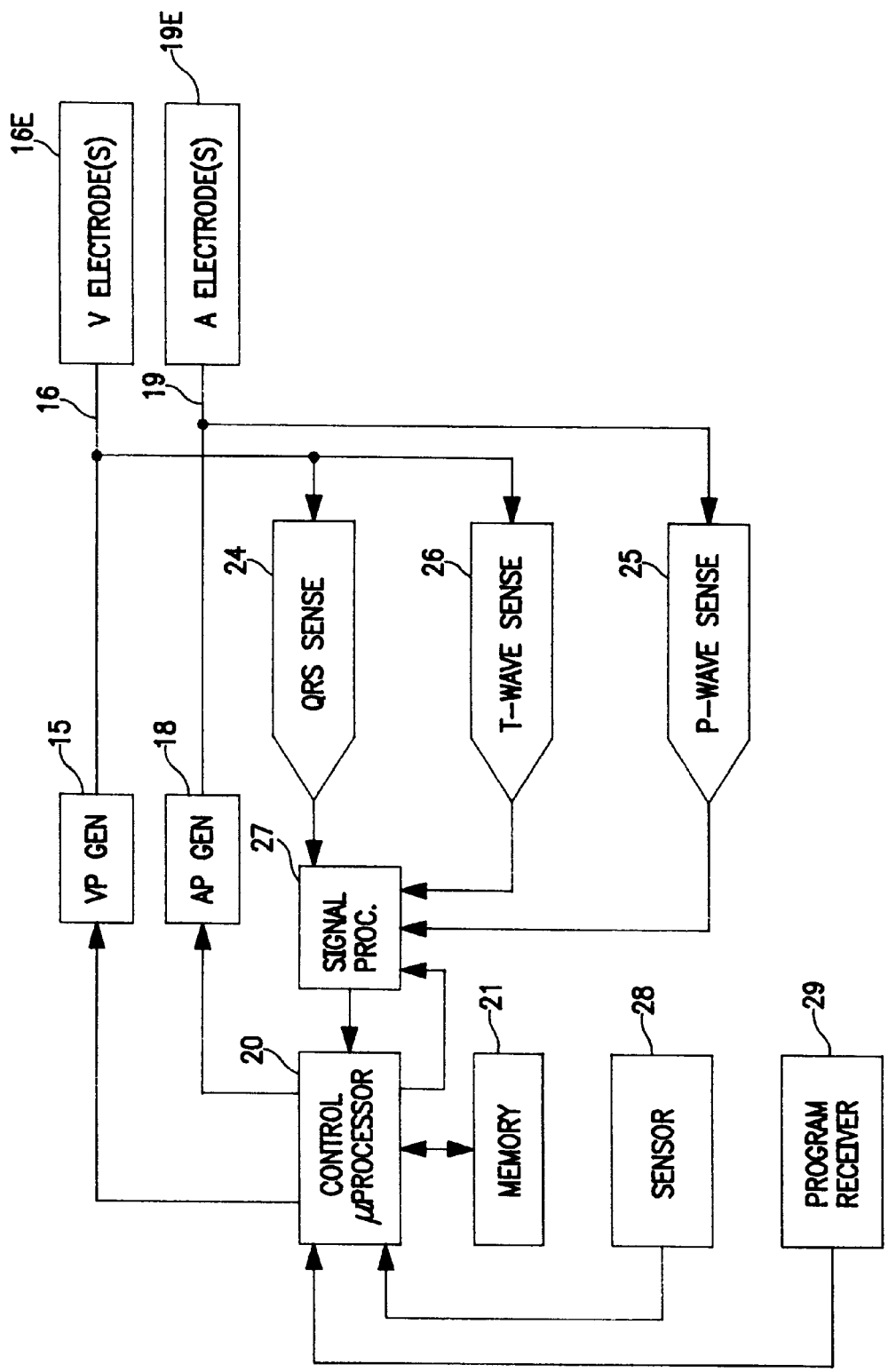
FIG. 1 is a block diagram illustrating the primary functional components of a pacemaker system in accordance with this invention.

Referring now to FIG. 1, there is shown a block diagram of the primary functional components of an illustrative pacemaker system for use in this invention. A VP generator 15 provides pacing pulses, generated under control of block 20, for delivery through lead 16 to one or more ventricular electrodes 16E located in the patient's right ventricle. Likewise, AP generator 18 provides atrial pacing pulses, also generated under control of block 20, for delivery through lead 19 to one or more atrial electrodes 1 9E located in the patient's right atrium. While not shown, it is understood that the invention is equally applicable to single chamber and to other multi-chamber configurations. Signals sensed by electrodes 1 6E are connected to QRS Sense circuit 24 which amplifies, the signals and provides V-Sense, or VS signals to signal processing block 27. Signals from ventricular electrodes 16E are also passed to T-Wave sense circuit 26, which provides T-Sense signals to block 27. Signals from atrial electrodes 19E are connected to P-Wave sense circuit 25, which outputs A-Sense, or AS signals to block 27.

Block 27 suitably contains dedicated signal processing hardware; and includes an A-D converter for converting the signals into digital form. The QRS and T-wave template generation and comparison steps, referred to below, are performed wholly or in part in this circuitry. The digital signals from block 27 are transferred to block 20 for further processing and/or storage. Block 20 controls the pacemaker functions, e.g., the cyclical functions of setting and timing out escape intervals; receiving sensed signals from the patient's heart and resetting escape intervals based on those signals; and carrying out special functions such as the VT Prevention function of this invention. Block 20 preferably comprises a microprocessor and associated memory, shown at 21, for storing the required software routines.

The memory 21 suitably includes dedicated RAM and ROM. Control parameters and values can be programmed from an external programmer through program receiver 29, in a known manner. The pacemaker can be programmed to operate in different modes. Sensor 28 may be used to provide a rate responsive parameter, e.g. activity, to be used alone or in combination with another parameter such as QT, in a manner known in the art.

Figure 2A:
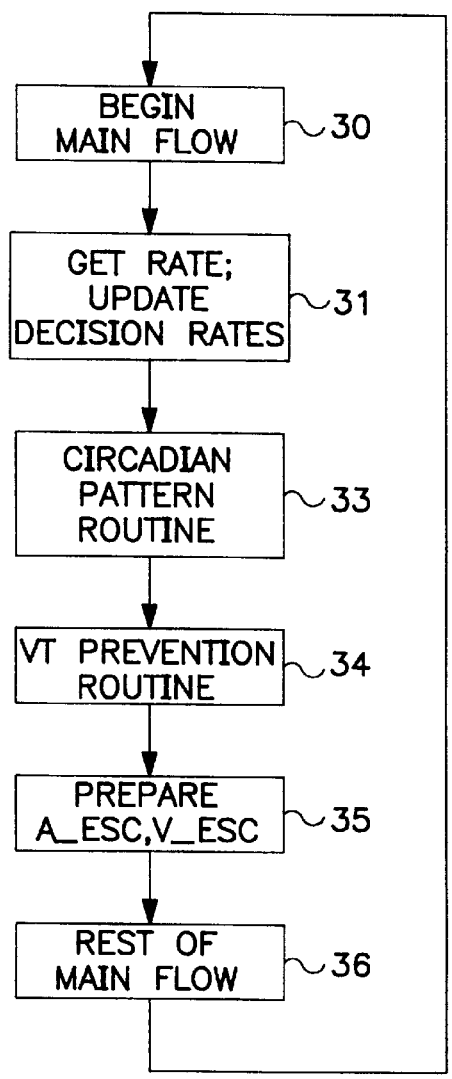
FIG. 2A is a simplified main flow diagram showing the steps pertinent to this invention which are taken each pacemaker cycle, and the relation of the VT prevention feature to the main operation routine.

Referring now to FIG. 2A there is provided a block diagram showing the place of the VT Prevention routine 34 within the overall main flow which is carried out cyclically. The main flow is entered cyclically at 30, where the pacemaker performs various bookkeeping and other steps. At 31, the spontaneous rate is determined; for a dual chamber system, decision rates are updated, in a manner as disclosed in U.S. Pat. No. 5,247,930, assigned to the assignee of this invention. At 33, the pacemaker carries out a routine for determining the patient's circadian pattern, in order to determine "daytime" and "nighttime" for the patient, and to determine the patient's awakening period. Then, at 34, the VT Prevention routine of this invention is performed, as discussed in detail below. If the result of this routine is the setting of an intervention rate in response to a determination of onset of VT, the intervention rate controls the setting of the ventricular escape interval. These atrial and ventricular escape intervals are set at 35, and at 36 the pacemaker carries out the rest of the main flow, including ventricular event handling. QRS and T-wave sensing is also done at block 36.

Figure 2B:
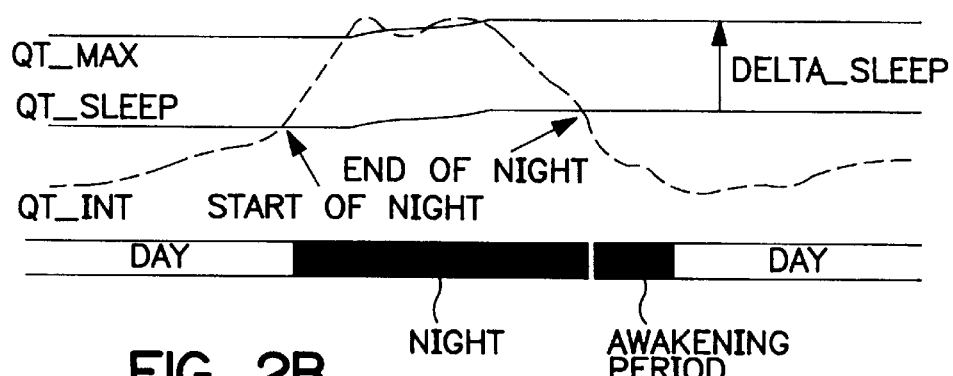
FIG. 2B is a timing diagram illustrating determination of night, end of night, and the awakening period by a circadian pattern routine.

Referring now to FIG. 2B, there is shown a timing diagram for determining the patient's circadian pattern, and in particular for determining the awakening period. Reference is made to U.S. patent application Ser. No. 08/800,413, filed Feb. 14, 1997, "Pacemaker With Automatic Lower Rate Limit Drop," herein incorporated by reference. The referenced disclosure sets forth several embodiments of pacemaker routines for determining when the patient enters nighttime and when the patient enters daytime, by monitoring and evaluating changes in QT interval. Transition from nighttime to daytime is shown as representing the start of the awakening period. The awakening period may suitably be determined in several ways. For example, the awakening period may be determined as extending from the nighttime/daytime transition for a period of, e.g., one hour. In this arrangement, the end of nighttime is suitably determined as the time when the QT interval drops below the variable QT_sleep, as shown in FIG. 2B. Alternately, in another embodiment, nighttime may be of a fixed duration, with the start of night being determined when the QT interval stays above the QT_sleep variable for a night_criterion duration. In this case, the awakening period may be set sodas to straddle the nighttime/daytime transition, e.g., from half an hour before to half an hour after. It is noted that other embodiments may be used for determining the end of night, e.g., by determining when the activity rate rises above a nighttime level.

Figure 3:
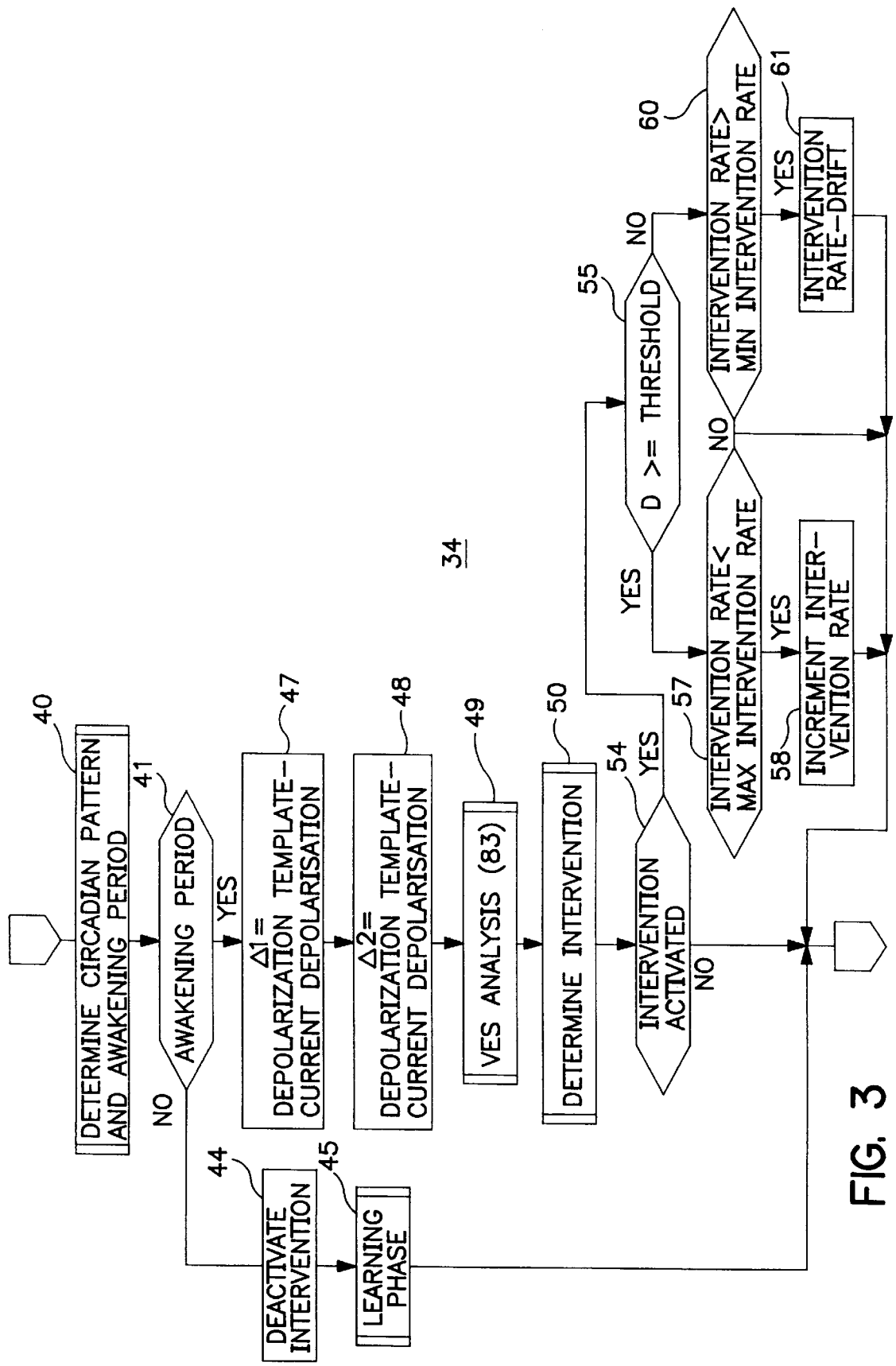
FIG. 3 is an overview flow diagram illustrating the cyclical operations of the VT Prevention routine in accordance with this invention.

Referring now to FIG. 3, there is shown a flow diagram of the specific steps taken in accordance with the VT prevention feature of this invention. At 40, the routine is run for determining the awakening period. At 41 the pacemaker determines whether the patient is in fact in the awakening period. If no, at 44 the intervention state is deactivated, and at 45 the pacemaker goes into the learning phase, the details of which are set forth in the connection with FIG. 4.

If the patient is in the awakening period, the pacemaker goes on to process current information concerning the depolarization (QRS) and repolarization (T wave) waveforms. At 47, the pacemaker obtains the depolarization template for the current cycle, and compares it to the depolarization template which was generated during the learning phase. The difference is computed and stored as Δ1. Likewise, at step 48, the pacemaker gets the current repolarization template and compares it with the stored repolarization template from the learning phase, and generates a Δ2, which is representative of the difference. Then, at block 49, the pacemaker goes through a VES analysis, to obtain a measure (Δ3) of whether there has been a ventricular extra systole, and how close the coupling interval was to the patient's mean QT interval. The VES analysis is set forth in particular detail in FIG. 5. Following this, the pacemaker goes to block 50, and determines whether intervention is indicated, based upon data gathered and generated at blocks 47, 48, and 49 above. The Determine Intervention routine is set forth in detail at FIG. 6.

Still referring to FIG. 3, at block 54, the pacemaker determines whether intervention has been activated. If no, the routine exits, and the pacemaker continues to set the pacing escape intervals in a normal way. However, if yes, the routine branches to block 55, and determines whether the variable D is equal to or greater than a predetermined threshold. D is calculated in the Determine Intervention routine 50, and represents a summation of the respective Δ values calculated at blocks 47, 48, which are representative of refractorines dispersion, and also the Δ value calculated at 49, which represents the presence of a dangerous VES. The calculation of D is discussed in more detail in connection with FIG. 6. If D is equal to or greater than threshold, at 57 the pacemaker determines whether the intervention rate remains less than the maximum intervention rate. If yes, intervention rate is incremented at 58; if no, intervention rate is at its maximum allowable value and the routine exits. If, at 55, D is not up to threshold, then at 60 it is determined whether the intervention rate is higher than the minimum intervention rate. If yes, at 61 intervention rate is decremented by subtracting a programmable drift value; if no, the intervention rate is as low as is allowed, and the routine exits.

Figure 4:
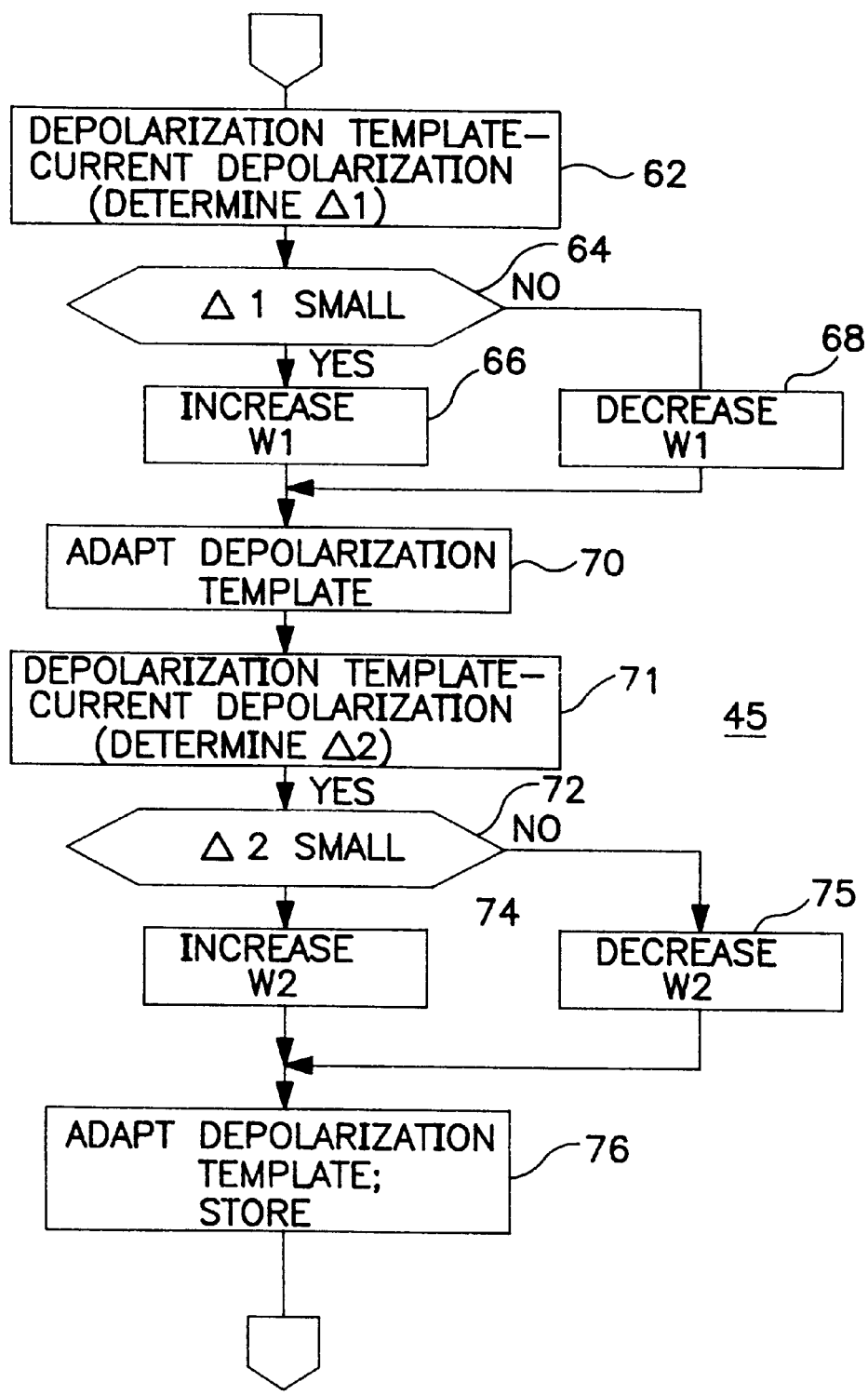
FIG. 4 is a simplified flow diagram illustrating the primary steps taken in carrying out the Learning Phase portion of the VT Prevention routine.

Referring now to FIG. 4, there is shown a flow diagram of the learning phase routine 45, in accordance with this invention. As discussed in connection with FIG. 3, this phase is entered when the patient is not in the awakening period. At 62, the pacemaker calculates a variable $\Delta 1$ which constitutes the depolarization template then stored in memory, minus the current depolarization template for the just detected R wave. In obtaining a template, the wave signal data is placed into digital form by an A-D converter, which is part of the function provided by signal processor block 27. Obtaining waveform templates is well known in the art, and any suitable hardware or software arrangement can be used in this invention. In a preferred embodiment, digital samples are obtained representing the waveform amplitude along successive time increments, from the beginning of the wave to the end, and are stored. In determining the $\Delta$ difference, the respective waveform amplitude values are subtracted, and the difference is integrated over the time domain. In a preferred embodiment, the template generation and template difference calculations are performed by dedicated hardware, as shown at 27. However, any combination of hardware and software can be utilized.

Next, at 64, it is determined whether the $\Delta 1$ value is small. The reason for making this determination is that large variations during the learning phase suggest that the signal is not stable enough to be a reference during the awakening period. Consequently, if the deviation found at 64 is statistically small (indicating stability), at 66 a weighting factor W1 is increased; if the deviation is not statistically small, then at 68 the W1 is decreased. These weighting factors are utilized in the subsequent determination of intervention in routine 50. Next, at block 70, the depolarization template is adapted so as to be changed toward the most recently detected depolarization template. This can be done, e.g., by matching the minimum values and slopes of the depolarization template and the new QRS wave, and adjusting each sample of the template incrementally toward the samples of the new QRS. The functions are suitably carried out by the microprocessor of block 20.

Still referring to FIG. 4, blocks 71, 72 and 74–76 represent corresponding steps for the repolarization template, which reflects the sensed T wave. At 71, the deviation $\Delta 2$ is determined, by subtracting the just obtained repolarization wave from the stored repolarization template. At 72, it is determined whether the deviation is small, representing a stable signal. If yes, weighting factor W2 is increased at 74; if no, W2 is decreased at 75. The repolarization template is then adapted and stored at 76.

Referring now to FIG. 5, there is shown a flow diagram of the routine 49 for carrying out VES analysis. This is done, as discussed above, because VT is often initiated or preceded by one or more ventricular extra-systoles if the patient heart rate is low enough and the coupling interval is critical, i.e., VES occurs near or in the vulnerable phase. In this situation likewise, intervention may be indicated, so the pacemaker of this invention collects VES data which is included in the Determine Intervention routine.

At block 82, it is determined whether there has been a VES. If no, the routine branches to block 83, and sets $\Delta 3$ (the deviation value corresponding to VES analysis) to zero. However, if there has been a VES, then it has to be determined how critical the VES is deemed, i.e., the deviation needs to be weighted. At 85, the pacemaker compares the coupling interval (the interval from the prior R wave to the VES) to the mean QT interval as stored. If the coupling interval minus the mean QT interval is less than or equal to a stored critical phase value, then the VES is deemed very critical, and at 90 $\Delta 3$ is given a weighted VERY_CRITICAL value. However, if the answer at 85 is no, then the routine goes to 86 and determines whether there have been a predetermined number n VES occurrences in the last m intervals, where n and m are programmable numbers. If yes, the VES occurrences is deemed critical, and at block 87 $\Delta 3$ is given a weighted CRITICAL value which is somewhat less than the VERY_CRITICAL value. If the answer at 86 is no, at 88 $\Delta 3$ is given a LOW_CRITICAL weighting. At routine 49, the values assigned to $\Delta 3$ include the weighting factor, such that the stored deviation is assumed to be accompanied by a weighting factor of I for the calculation which is carried out at block 77.

Referring now to FIG. 6, there is shown a flow diagram of the Determined Intervention routine 50. At step 77, the pacemaker determines the total deviation D, which is calculated by taking the sum of all the separate deviations, each multiplied by its respective weighting factor W. In the preferred embodiment as illustrated, there are three different deviations determined, so the summation is from i=1 to i=3. Thus, each cycle the summation constitutes $\Delta 1$ multiplied by the current value of W1; $\Delta 2$ multiplied by the current value of W2, and the determined value of $\Delta 3$, where the weighting factor is 1 since the value of $\Delta 3$ has already been calculated to reflect appropriate weighting. At 78, it is determined whether the current value D is greater than or equal to threshold. If no, intervention is not indicated and the routine exits. However, if D is greater than or equal to the programmed threshold, then intervention is activated at step 80, suitably by setting a flag to store the fact that intervention has been activated. As seen in FIG. 3, once intervention has been activated, it is not deactivated until the awakening period is over, at which time the pacemaker proceeds to block 44 and deactivates intervention. As per the above discussion of FIG. 3, if D drops below threshold when Intervention is activated, the Intervention rate is decremented toward a lower limit.

Recapitulating, and referring to FIG. 3, it is seen that during normal periods outside of the awakening period, both daytime and nighttime, the pacemaker is continually adapting the depolarization and repolarization templates in the learning phase. When the patient is in the awakening period, data represented by deviation values $\Delta 1$, $\Delta 2$ and $\Delta 3$ are obtained at blocks 47, 48 and 49 respectively. Whenever, during the awakening period, the cumulative sum of the deviations exceeds a predetermined threshold, intervention is activated, and the intervention mode is maintained throughout the awakening period. Of course, if the deviation values, which represent refractory dispersion, become small, then the intervention rate drifts down to a lower rate limit, such that there effectively is no overdrive intervention. However, as long as the wave variability remains high, the intervention rate will be maintained so as to provide overdrive pacing calculated to prevent ventricular tachycardia.

It is noted that while three separate deviation measurements are illustrated in the preferred embodiments, additional data can be collected, and weighted accordingly. Thus, each cycle a direct measure of QTc or $QT_c$ can be obtained and a value of QT dispersion calculated and weighted; this weighted QT dispersion value is then added to the calculation made for determining intervention. Additionally, each weighting factor can be programmed to vary within predetermined limits, so that weighting can be adapted in terms of known patient history.

What is claimed is:

1. A cardiac pacemaker system for pacing a patient, having VP means for generating and delivering ventricular pacing pulses to a patient's ventricle, VS means for sensing ventricular QRS and T waves, rate means for determining the patient's spontaneous heart rate, and control means for controlling when said VP means generates and delivers ventricular pacing pulses and the pacing rate of such pulses, wherein said control means further comprises VT prevention means for controlling said VP means to deliver pacing pulses at a rate overriding the patient's spontaneous rate when a threshold of refractory dispersion is detected during patient awakening, said VT prevention means comprising:

awakening means for determining an awakening period when the patient is awakening;

depolarization means for determining a first measure of dispersion of the patient's depolarization wave during awakening;

repolarization means for determining a second measure of dispersion of the patient's repolarization wave during awakening; and intervention means for controlling said VP means to generate and deliver pacing pulses at an intervention rate that overrides the patient's spontaneous rate as a function of said first and second measures.

2. The system as described in claim 1, wherein said VT prevention means comprises learning means operative during the patient's non-awakening period for generating and storing reference signals representative of the patient's depolarization and repolarization waves during said non-awakening period, and current means for obtaining current signals representative of said depolarization and repolarization signals during said awakening period.

3. The system as described in claim 2, wherein said learning means comprises template means for obtaining and storing reference depolarization and repolarization templates, and said current means comprises current template means for cyclically obtaining and storing current depolarization and repolarization templates.

4. The system as described in claim 3, wherein said depolarization means comprises first comparison means for comparing the current depolarization template with said reference depolarization template to obtain a depolarization deviation value, and said repolarization means comprises second comparison means for comparing the current repolarization template with said reference repolarization template to obtain a repolarization deviation value.

5. The system as described in claim 4, wherein said depolarization means comprises first weighting means for weighting said depolarization deviation value as a function of depolarization wave stability to obtain said first measure, and said repolarization means comprises second weighting means for weighting said repolarization deviation value as a function of repolarization wave stability to obtain said second measure.

6. The system as described in claim 1, further comprising VES means for obtaining data representative of each patient ventricular extra systole and its criticality with respect to the ventricular vulnerable period.

7. The system as described in claim 1, wherein said VT prevention means further comprises means operative during said awakening period for accumulating weighted data representative of depolarization dispersion and repolarization dispersion.

8. A cardiac pacemaker system for pacing a patient, having VP means for generating and delivering ventricular pacing pulses to a patient's ventricle, VS means for sensing ventricular QRS and T waves, rate means for determining the patient's spontaneous heart rate, and control means for controlling when said VP means generates and delivers ventricular pacing pulses and the pacing rate of such pulses, wherein said control means further comprises VT prevention means for controlling said VP means to deliver pacing pulses at a rate overriding the patient's spontaneous rate when a threshold of refractory dispersion is detected during patient awakening, said VT prevention means comprising:

awakening means for determining an awakening period when the patient is awakening;

dispersion data means for determining during said awakening period data representative of ventricular refractory dispersion;

threshold means for determining from said data when patient refractory dispersion exceeds said threshold; and overdrive control means for setting pacing rate at an intervention rate which is adjusted as a function of said data.

9. The system as described in claim 8, wherein said dispersion data means comprises first means for obtaining data representative of a first predetermined parameter of the QRS-T wave signals and second means for obtaining data representative of a second predetermined parameter of the QRS-T wave signals.

10. A pacemaker system for pacing a patient's heart, having VP means for generating and delivering pacing pulses to a patient's ventricle, rate control means for controlling the rate of said pacing pulses, and said rate control means having VT prevention means for controlling said rate to an intervention rate when said patient has a detected measure of refractory dispersion during awakening, said VT prevention means comprising:

awakening means for determining when said patient is in a state of awakening;

dispersion means for determining a measure of dispersion of ventricular refractoriness; and intervention means for setting and continually adjusting said intervention rate as a function of said dispersion measure.

11. The system as described in claim 10, wherein said dispersion means comprises means for cyclically obtaining a measure of the variability of the patient's QRS during the awakening state.

12. The system as described in claim 10, wherein said dispersion means comprises means for obtaining a reference measure of the patient's QRS waveform when the patient is not awakening, means for obtaining a current measure of the patient's current QRS waveform during awakening, and comparing means for comparing said current measure with said reference measure.

13. The system as described in claim 10, wherein said dispersion means comprises means for cyclically obtaining a measure of the variability of the patient's T wave during the awakening state.

14. The system as described in claim 10, wherein said dispersion means comprises means for obtaining a reference measure of the patient's T wave when the patient is not awakening, means for obtaining a current measure of the patient's current T wave during awakening, and comparing means for comparing said current measure with said reference measure.

15. The system as described in claim 10, wherein said dispersion means comprises QT means for cyclically obtaining a measure of the variability of the patient's QT interval during the awakening state.

16. The system as described in claim 10, further comprising VES means for detecting when a ventricular extra systole occurs during the awakening state that is close to the end of the ventricular refractory period, and wherein said intervention means comprises determining means for determining said intervention rate as a function of said VES detecting.

17. The system as described in claim 10, wherein said dispersion means comprises means for obtaining at least two respective measures of said dispersion, and accumulating means for accumulating said measures, and wherein said intervention means adjusts said intervention rate as a function of said accumulated measures.

18. The system as described in claim 10, comprising rate means for determining the patient's spontaneous rate, and wherein said VT prevention means comprises means for setting said intervention right higher than said spontaneous rate, whereby said pacemaker overdrives the patient's spontaneous rate during said awakening state.

19. The system as described in claim 17, wherein said intervention means comprises increment means for incrementing said intervention rate when said accumulated measures increase, and for decrementing said intervention rate when said accumulated measures decrease.

20. The system as described in claim 10, wherein said dispersion means comprises data means for cyclically obtaining data representative of ventricular refractoriness.

* * * * *